March 1, 1955 V. ASSERETTO Plant Pat. 1,356
ROSE PLANT
Filed June 29, 1953
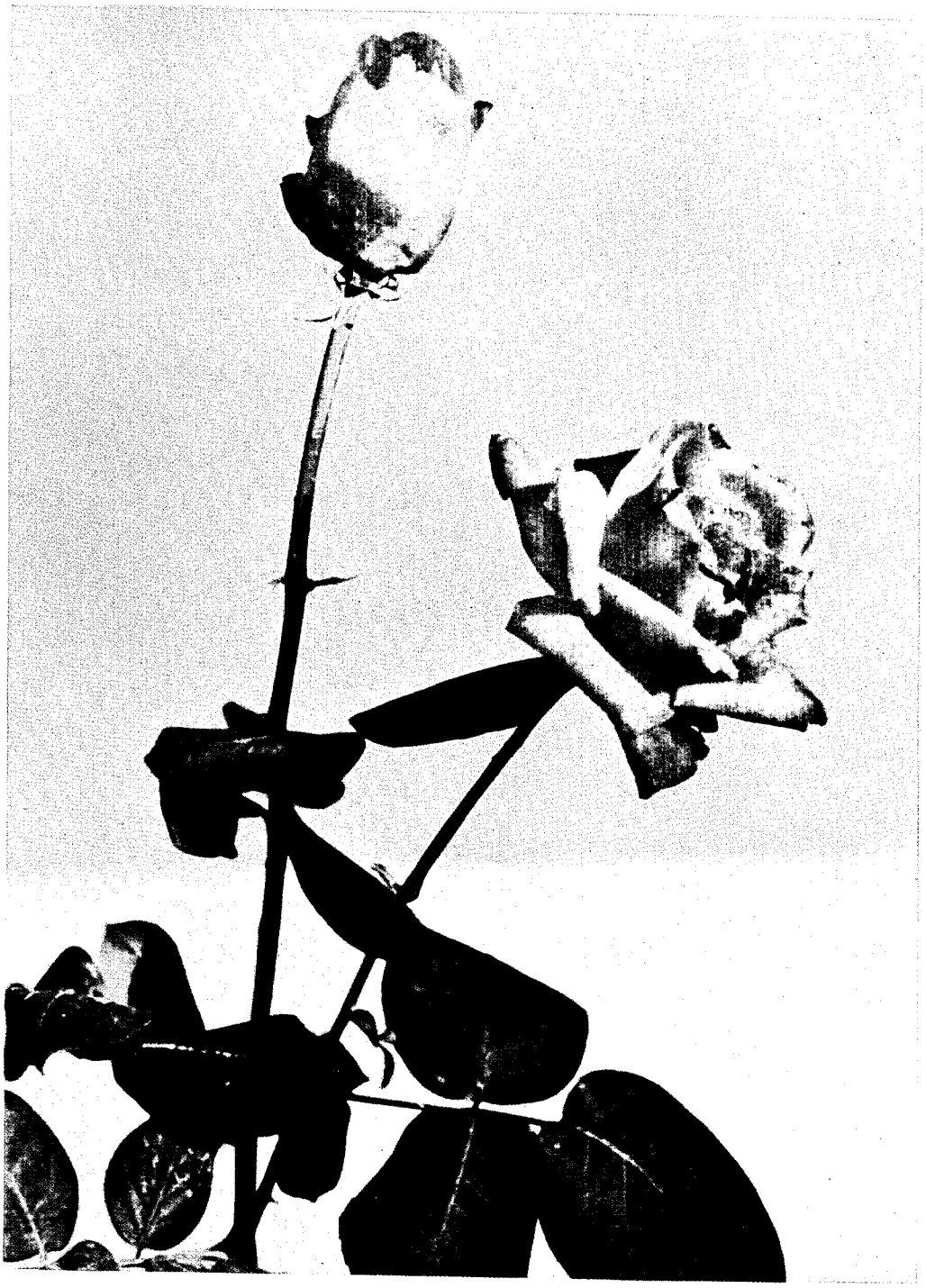
Inventor.
V. Asseretto
By: Robb & Robb, Attys.

United States Patent Office

Plant Pat. 1,356
Patented Mar. 1, 1955

1,356

ROSE PLANT

Vincenzo Asseretto, San Remo, Italy

Application June 29, 1953, Serial No. 364,979

Claims priority, application Italy February 21, 1953

1 Claim. (Cl. 47—61)

The present invention relates to a new and distinct variety of rose plant of the hybrid tea class, which originated as a sport of the variety "Rome Glory" (Plant Patent No. 304). The new sport was discovered by me in my nurseries at San Remo, Italy, among cultivated plants of "Rome Glory" which I was growing. In making this discovery, my attention was directed to a plant of "Rome Glory" which had produced flowers substantially different in color from the true color of the flowers of "Rome Glory," whereupon, I examined the plant carefully and found that the "Rome Glory" parent plant had sported. Thereafter, I carefully preserved the sport and promptly took steps to asexually reproduce the same in order to develop it and ascertain whether the new characteristic of the bloom was permanently established and transmissible by asexual reproduction.

In the course of asexually reproducing the new variety by budding at San Remo, Italy, I found that the new variety was not only distinguished from its parent "Rome Glory" by the Fuchsin Red color of its blooms, as compared with the Scarlet Red of "Rome Glory" blooms, but I also found that it has other important and desirable characteristics which distinguish it from its parent, as well as from all other varieties of its class, the most outstanding features being as follows:

(1) My new variety is particularly hardy and resistant to both cold and hot weather, as well as to diseases;

(2) It is endowed with great vigor and is exceptionally free-blooming, thus making it especially suitable for the cut-flower industry, as well as for growing outdoors;

(3) The flowers are relatively large in size and are exceptionally long-lasting both as cut flowers and when left on the plant;

(4) The brilliant Fuchsin Red general color tonality of the flowers is exceedingly distinctive and attractive, especially when considered in combination with the other outstanding characteristics of the variety;

(5) The foliage is relatively large in size and larger than that of "Rome Glory"; and (6) The shape of the flower buds is quite distinctive and substantially different from that of the buds of "Rome Glory."

The accompanying drawing shows typical specimens of the flowers, foliage and stems of my new variety in different stages of development.

The following is a detailed description of my new variety, with color terminology in accordance with the French Repertoire Des Couleurs by Rene Oberthur, issued by the Societe Francaise Des Chrysanthemistes (1905 Standard Edition), except where general color terms of ordinary dictionary significance are obvious:

Parentage: Sport of "Rome Glory."
Classification:
*Botanic.*—Hybrid tea.
*Commercial.*—Hybrid tea.

FLOWER (Observations made from plants grown in my nursery at San Remo, Italy.)

Blooming habit: Recurrent—continuous.
Bud:
*Size.*—Large.
*Form.*—Ovoid, but more open at the end like a vase or urn.
*Color.*—When sepals first divide—Reddish Purple, Tab. 161/4. When sepals begin to unfurl—Fuchsin Red, Tab. 160/3. When half blown—Fuchsin Red, Tab. 160/2. Inside of petals—Fuchsin Red, Tab. 160/1-2. Reverse of petals—Reddish Purple, Tab. 161/2-3.
*Sepals.*—Smooth edge; velvety surface; curl back when bud unfurls.
*Calyx.*—Shape—funnel. Size—medium. Aspect—smooth. Strength—erect. Color—Moss Green, Tab. 272/1.
*Opening.*—Opens well; is not affected by adverse weather conditions.

Bloom:
*Size.*—Large.
*Borne.*—Singly.
*Stems.*—Long; hard; strong.
*Form.*—Globular, but opening in a point like a vase or urn.
*Petalage.*—Double; about 20 to 35 petals under usual conditions.
*Color.*—Center of flower—Fuchsin Red, Tab. 160/1. Outer petals—Fuchsin Red, Tab. 160/1. Base of petals—Yellow spot. Inside of petals—Fuchsin Red, Tab. 160/1. Reverse of petals—Fuchsin Red, Tab. 160/1. General color tonality from a distance—Brilliant Fuchsin Red, Tab. 160/1.
*Variegations.*—None.
*Discoloration.*—No discoloration for many days; slight paling after 5 to 6 days.
Petals:
*Texture.*—Medium thickness; not appreciably affected by wet or hot weather.
*Appearance.*—Inside—satiny. Outside—satiny.
*Form.*—Round, with outer edge curling back.
*Arrangement.*—Regular; imbricated.
*Petaloids in center.*—Few; well-expanded.
*Persistence.*—Very long.
*Fragrance.*—Medium intensity. Nature—Tea Rose perfume.
*Lasting quality.*—Very long, both on the plant and as cut flowers.

REPRODUCTIVE ORGANS

Stamens: Numerous; separated.
Anthers: Large. Color—yellow.
Threads: Long.
Pollen: Color—gold yellow.
Styles: Numerous; growing spirally when the bud is closed; separated when the flower opens.
Stigma: Well-open; funnel-shaped. Color—white.
Ovaries: Well-developed; do not protrude from calyx.
Fruit:
*Form.*—Cup-shaped; round edged.
*Aspect.*—Smooth.
*Sepals.*—Caducous.
*Color at maturity.*—Orange red.

PLANT

Form: Bush.
Growth: Free-growing; vigorous.
Foliage: Compound of 3, 5 or 7, but generally 5, leaflets.
*Size.*—Medium-large.
*Quantity.*—Abundant.
*Color.*—Upper side—Cypress Green, Tab. 284/3-4. Under side—Dark Grey Green, Tab. 277.
*Shape.*—Round-oval, with a slight point.
*Texture.*—Upper side—smooth. Under side—velvety.
*Ribs and veins.*—Prominent.
*Edge.*—Finely serrated.
*Serration.*—Small.
*Rachis.*—Long; strong. Color: Upper side—dark green; under side—light green.
*Disease resistance.*—Good resistance to common diseases, as determined by comparison with other varieties grown under comparable cultural conditions at San Remo, Italy.
Wood:
*New wood.*—Color—Cypress Green, Tab. 248/2-3.
*Old wood.*—Color—brownish green.
Thorns:
*Quantity.*—Medium number on old wood; few on floral stalks.

*Form.*—Large base; medium length; slightly hooked downward.

*Color.*—Light green; nearly transparent.

*Prickles.*—None.

*Short needles.*—None.

I claim:

A new and distinct variety of rose plant of the hybrid tea class, substantially as herein shown and described, characterized particularly as to novelty by its hardiness and resistance to cold and hot weather and to diseases, by its exceptionally vigorous and free-blooming habits of growth, by the relatively large size and long-lasting quality of its flowers both as cut flowers and when left on the plant, by the distinctive brilliant Fuchsin Red general color tonality of its flowers, by the distinctive shape of its flower buds, by the relatively large size of its foliage, and by its general suitability for industrial culture under glass as well as for outdoor culture.

No references cited.